United States Patent [19]

Mitscher et al.

[11] 4,229,592
[45] Oct. 21, 1980

[54] INTERMEDIATE FOR PROSTAGLANDINS AND PROCESS FOR PREPARING THE INTERMEDIATE

[75] Inventors: Lester A. Mitscher; George W. Clark, III; Paul B. Hudson, all of Lawrence, Kans.

[73] Assignee: Kansas University Endowment Association, Lawrence, Kans.

[21] Appl. No.: 875,064

[22] Filed: Feb. 6, 1978

[51] Int. Cl.$^2$ ............... C07C 67/08; C07C 67/28; C07C 69/145

[52] U.S. Cl. .................. 560/231; 204/158 HE; 560/238; 560/240; 568/379

[58] Field of Search .............. 560/231; 260/586 R

[56] References Cited

U.S. PATENT DOCUMENTS

| | | | |
|---|---|---|---|
| 4,027,036 | 5/1977 | Dawwon et al. | 560/231 |
| 4,056,562 | 11/1977 | Mueller | 560/231 |
| 4,103,091 | 7/1978 | Mitscher et al. | 560/231 |

Primary Examiner—Vivian Garner
Attorney, Agent, or Firm—Paul D. Burgauer; Robert L. Niblack

[57] ABSTRACT

The compound of the formula

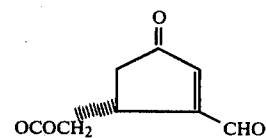

has been found to be an important and practical intermediate with the proper stereo-isomerism for the preparation of numerous prostaglandin derivatives. It can easily be converted to 4α-acetoxy-2-cyclopentenone by a variety of processes.

4 Claims, No Drawings

INTERMEDIATE FOR PROSTAGLANDINS AND PROCESS FOR PREPARING THE INTERMEDIATE

DETAILED DESCRIPTION OF THE INVENTION

This invention is directed to a new intermediate which is a precursor in the synthesis of prostaglandin derivatives in the established PG-synthesis of Kurzumi, et al., Tetrahedron 32, 1713 (1976). The new compound, 4α-acetoxy-2-cyclopentenone-3-carboxyaldehyde (I) does not lose its optical configuration upon cleavage of the aldehyde group; it has the further advantage of being available through conversion of a naturally occurring starting material having the proper stereochemistry and can be isolated substantially without contamination by undesired optical isomers.

The new compound I is prepared by partially acetylating terrein in the 5-position to III, removing the entire acetoxy group at 5 (IV), acetylating the hydroxy in the 4-position (V), and oxidizing the propylene chain at the 3-position to the aldehyde group. Schematically, the procedure is depicted as follows:

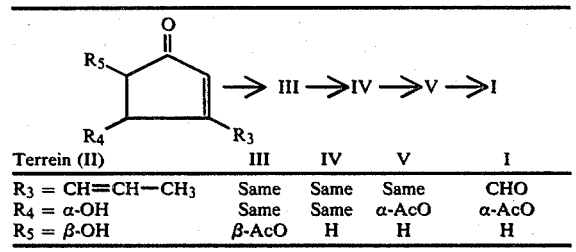

| | Terrein (II) | III | IV | V | I |
|---|---|---|---|---|---|
| $R_3$ = | $CH=CH-CH_3$ | Same | Same | Same | CHO |
| $R_4$ = | α-OH | Same | Same | α-AcO | α-AcO |
| $R_5$ = | β-OH | β-AcO | H | H | H |

In brief, the process involves the removal of the 5-hydroxy group of terrein followed by acetylation and subsequent oxidation of the 3-propylene group to the aldehyde group.

More specifically, terrein is treated with acetic anhydride and sodium acetate to form III. This can be done selectively by carrying out the reactions at a temperature below 65° C. Completion of this step requires 1–3 days but at the indicated temperature, the hydroxy group in the 4-position remains unaffected. The end point can easily be determined by the use of thin layer chromatography. In turn, III is treated with chromous chloride to produce IV. IV is also acetylated with acetic anhydride and sodium acetate and the resulting V is treated with osmium tetroxide and alkali metal periodate to produce I. Alternately, compound V can be converted to I by use of ozone or alkali metal periodate and potassium permanganate or equivalent double-bond cleaving oxidative reactions commonly employed by those skilled in the art. Mostly, these reactions are carried out in an inert liquid medium, i.e., an organic solvent that does not react with the starting material, the end product or the oxidizing agent.

In order to convert I to the known and highly useful PG starting material used by Kurzumi, et al., 4α-acetoxy-2-cyclopentenone, I is treated with tris(triphenylphosphine)rhodium chloride which removes the aldehyde group. Alternate reagents for the decarbonylation include palladized charcoal, iron carbonyl or ultraviolet irradiation. One can also reduce the keto group to the corresponding hydroxy group with zinc borohydride after protecting the aldehyde as an acetal group, remove the aldehyde group in the above fashion and reoxidize the hydroxy group to the original keto group with chromium trioxide in acetone to produce VI. The conversion of I to VI can also be accomplished by oxidizing the aldehyde group with Jones' reagent to the corresponding carboxylic acid group. Upon forming the acid chloride, the latter can be esterified with t-butylhydroperoxide, forming the butyl perester which, upon heating in cumene, converts to VI.

In order to illustrate the preparation and use of the new compound, reference is made to the following specific examples, which are not be understood as limiting the scope of this invention. In these examples, all parts are by weight unless specified otherwise.

EXAMPLE 1

(a) To a solution of 499.2 parts of terrein in 15 parts of tetrahydrofuran (THF) was added 500 parts of sodium acetate and 314.2 parts of freshly distilled acetic anhydride. This mixture was stirred for 3 days at room temperature. The solvents were then evaporated under reduced pressure and the remaining white solid was washed with 150 parts of ether and 50 parts of chloroform. The residue was filtered, evaporated and dried in vacuo to afford a clear oil which slowly crystallized on standing. After recrystallization from hexane, 306.4 parts of clear needles of 5-acetyl-terrein (III) melting at 96.5°–97° C. were obtained.

(b) A solution of 1.025 parts of III in 80 parts of acetone was stirred in a nitrogen atmosphere for 15 minutes and then titrated with a chromous chloride solution prepared according to Djerassi et al., J. Am. Chem. Soc. 72, 4077 (1950) until TLC analysis showed the absence of III. The blue solution was then diluted with 80 parts of a saturated NaCl solution and extracted with 2 portions of 100 parts each and then with 2 portions of 50 parts each of chloroform. The organic layer was dried over magnesium sulfate, filtered and evaporated to afford 0.7313 parts of 5-desoxyterrein (IV) as a clear, yellow oil.

(c) A solution of 0.7104 parts of IV in 10 parts of THF was treated with 10 parts of acetic anhydride and 3.5 parts of sodium acetate at 55°–60° C. for 17 hours and then diluted with 55 parts of a saturated aqueous NaCl solution. The mixture was extracted and dried as in (b) and concentrated in vacuo. Excess acetic anhydride was removed by repeated evaporations with carbon tetrachloride and the last traces were eliminated by overnight drying in vacuo. A crude yield of 0.859 parts of 5-deoxy-4α-acetylterrein (V) in the form of a white solid was obtained. After recrystallization from hexane, V was obtained in white needles melting at 49°–50° C.

(d) To a solution of 0.768 parts of V in 50 parts of acetone and 8 parts of water was added 1 part of a 4% aqueous solution of osmium tetroxide. The solution turned brown upon stirring. Under rapid stirring, 2.737 parts of sodium periodate was added, clearing the solution slowly and forming a white precipitate. Stirring was continued for 2 hours until the absence of V could be established by TLC. The solution was then filtered and the residue was washed with several portions of acetone. After combining the filtrate and wash liquors, the solvent was evaporated. The residue was leached with chloroform and the filtrate was dried over magnesium sulfate, filtered and evaporated to yield 0.5204 parts of a yellow solid. Recrystallization from hexane gave prisms of 4α-acetoxy-2-cyclopentenone-3-carboxaldehyde (I), melting at 99°–100°.

EXAMPLE 2

The solution was prepared from 124.5 parts of the aldehyde I of Example 1(d) in 6 parts of butyryl nitrile. To this solution, 705 parts of tris(triphenylphosphine)rhodium chloride was added. The red solution was refluxed at 120° C. until I could no longer be detected by TLC. After 1 hour, the dark brown mixture was cooled, the solvent was removed under reduced pressure below 45° C. and the black residue was taken up in ethanol. After filtration, the ethanol was evaporated at 45° C. under reduced pressure and the residue was chromatographed on two 20 cm×2 cm×2 mm silica gel plates with ethyl acetate: hexane 3:2(vol.), requiring two developments. The top half of the plates were removed and washed with ethyl acetate which afforded 26 parts of a yellow oil. This oil was chromatographed on a 10 cm×20 cm×0.25 mm silica gel plate using the above EtOAc/hexane mixture. The most intense band under UV light was isolated and identified as 4α-acetoxy-2-cyclopentenone. It is a clear oil.

EXAMPLE 3

(a) A solution of 0.731 parts of I in 100 parts acetone was cooled to 0° C. and 0.8 parts. of 8N-Jones' reagent was added using rapid stirring for 1 hour. The chromium salts were removed by filtration and washed with acetone. The filtrate was evaporated and the residue was taken up in 100 parts of chloroform. The latter is extracted with three 25 part portions of a saturated aqueous sodium bicarbonate solution. After acidifying the combined extracts to pH 1 with hydrochloric acid, extracting with four 50 part portions of ethyl acetate, separating, drying, filtering and evaporating the organic layer, 0.7447 parts of 4α-acetoxy-2-cyclopentenone-3-carboxylic acid, m.p. 133°–5° C. was obtained.

(b) A solution of 0.2125 parts of the above acid in 40 parts of methylene chloride was cooled to 0° C. before adding 1 part of oxalyl chloride and a catalytic amount of DMF. Rapid stirring, first at 0°, and for 3 hours at room temperature was followed by evaporation of the solvents at room temperature under reduced pressure. A dark oil was obtained which was redissolved in 40 parts of methylene chloride. The solution cooled to 0° C. and a mixture of 0.18 parts of t-butylhydroperoxide and 0.160 parts of pyridine in 10 parts of methylene chloride was dropwise added with stirring. After rapid stirring for 1 hour in an ice bath and 3 hours at room temperature, the reaction mixture was washed with water (2×50 parts), 50 parts of 10% HCl and finally with 50 parts of saturated aqueous sodium bicarbonate. The organic layer was dried, filtered and evaporated under reduced pressure at room temperature to produce the desired perester.

(c) A solution of 0.1438 parts of the above perester in 8 parts of cumene was heated in an oil bath to 160° C. for 18 hours during which time $CO_2$ evolved and was trapped in a barium hydroxide solution. The solvent was then removed by short-path distillation at 60° C./40 mm. to separate the desired 4α-acetoxy-2-cyclopentenone in crude form ($R_f$ 0.48; silica gel; ethyl acetate/hexane 3:2).

In all the above intermediates, the nmr, UV- and IR-spectra were consistent with the assigned structures.

While the above method for making the new compound I is only one of a number of variations to produce a significant starting material for prostaglandins having the necessary optical configuration, other methods can also be used to produce VI. As seen above, the current method of producing said material is simple and strictly chemical in nature while previous methods involved biological transformations with appropriately low yields and time consuming procedures. Neverless, the current method assures the manufacture of I wherein the acetoxy substituent is in the required α-position.

I claim:
1. 4α-acetoxy-2-cyclopentenone-3-carboxyaldehyde.
2. The method of preparing 4α-acetoxy-2-cyclopentenone-3-carboxyaldehyde consisting essentially in acetylating terrein in the 5-position with acetic anhydride and sodium acetate at a temperature below 65° C., removing the acetoxy group of the formed 5-acetylterrein with chromous chloride, acetylating the formed 5-deoxyterrein with acetic anhydride and sodium acetate and cleaving the side chain of the formed 5-deoxy-4α-acetylterrein through oxidation of the side-chain double bond to said aldehyde in the named stereoconfiguration.
3. The method of claim 2 wherein said oxidation is carried out in the presence of osmium tetroxide and an alkali metal periodate in the presence of an inert organic solvent.
4. The method of claim 3 wherein said inert solvent is acetone.

* * * * *